United States Patent
Singhal

(10) Patent No.: US 9,924,892 B2
(45) Date of Patent: Mar. 27, 2018

(54) INTEGRATED BLOOD GLUCOSE MEASURING DEVICE

(76) Inventor: Tara Chand Singhal, Torrance, CA (US)

( * ) Notice: Subject to any disclaimer, the term of this patent is extended or adjusted under 35 U.S.C. 154(b) by 53 days.

(21) Appl. No.: 13/134,148

(22) Filed: May 31, 2011

(65) Prior Publication Data

US 2012/0310114 A1 Dec. 6, 2012

(51) Int. Cl.
*A61B 5/145* (2006.01)
*A61B 5/1468* (2006.01)
*G01N 33/487* (2006.01)

(52) U.S. Cl.
CPC ........ *A61B 5/14532* (2013.01); *A61B 5/1468* (2013.01); *G01N 33/48757* (2013.01)

(58) Field of Classification Search
USPC .......................... 600/583, 584; 606/181, 182
See application file for complete search history.

(56) References Cited

U.S. PATENT DOCUMENTS

| | | | |
|---|---|---|---|
| 5,971,941 A * | 10/1999 | Simons et al. | 600/573 |
| 7,303,726 B2 * | 12/2007 | McAllister et al. | 422/68.1 |
| 7,922,971 B2 * | 4/2011 | Bryer et al. | 422/50 |
| 8,062,235 B2 * | 11/2011 | Planman et al. | 600/584 |
| 2002/0076349 A1 * | 6/2002 | Aitken | G01N 33/48757 422/430 |
| 2003/0185705 A1 * | 10/2003 | Otake | G01N 33/48757 422/404 |
| 2003/0191415 A1 * | 10/2003 | Moerman et al. | 600/584 |
| 2005/0143675 A1 | 6/2005 | Neel | |
| 2005/0186162 A1 * | 8/2005 | Sato | G01N 33/48757 424/63 |
| 2007/0173739 A1 | 7/2007 | Chan | |
| 2007/0264165 A1 * | 11/2007 | Chan | B65D 83/0829 422/400 |
| 2007/0293790 A1 * | 12/2007 | Bainczyk | G01N 33/48757 600/583 |
| 2008/0089812 A1 * | 4/2008 | Uehata | G01N 33/48757 422/400 |

(Continued)

FOREIGN PATENT DOCUMENTS

EP   1 362 551 A1   11/2003
EP   2157428 A2 *   2/2010   ......... G01N 27/3273

(Continued)

OTHER PUBLICATIONS

PCT Partial Search Report PCT/US2012/034011 dated: Jul. 4, 2012, pp. 4 and 5.

*Primary Examiner* — Sean Dougherty
(74) *Attorney, Agent, or Firm* — Steve Roeder, Esq.

(57) ABSTRACT

An integrated blood glucose measuring device is described that has blood glucose metering device, a glucose metering test strip storage mechanism attachable to the metering device, a test strip feeding mechanism for feeding a single test strip from the storage mechanism for blood intake. The metering device, the test strip storage mechanism and the test strip feeding mechanism are integrated into a single device for blood glucose measurement. In another embodiment, a lancet mechanism is attachable to a side of the metering device and thus the metering device, the storage mechanism, the test strip feeding mechanism, and the lancet mechanism are integrated into a single device for blood glucose measurement.

20 Claims, 7 Drawing Sheets

(56) References Cited

U.S. PATENT DOCUMENTS

| | | | |
|---|---|---|---|
| 2008/0167578 A1* | 7/2008 | Bryer et al. | 600/583 |
| 2008/0217354 A1* | 9/2008 | Newman | B65D 83/0829 221/229 |
| 2009/0270765 A1* | 10/2009 | Ghesquiere et al. | 600/583 |
| 2010/0025270 A1* | 2/2010 | Surridge | G01N 27/3273 206/305 |
| 2010/0087754 A1* | 4/2010 | Rush et al. | 600/583 |
| 2010/0286563 A1* | 11/2010 | Bryer et al. | 600/583 |
| 2011/0040165 A1* | 2/2011 | Williams, III | A61B 5/157 600/365 |
| 2011/0077478 A1* | 3/2011 | Freeman et al. | 600/309 |

FOREIGN PATENT DOCUMENTS

| | | | | |
|---|---|---|---|---|
| JP | 2003337132 A | * | 11/2003 | ....... G01N 33/48757 |
| JP | 2008216258 A | * | 9/2008 | ........ B65D 83/0829 |
| JP | 2008224667 A | * | 9/2008 | ....... G01N 33/48757 |

* cited by examiner

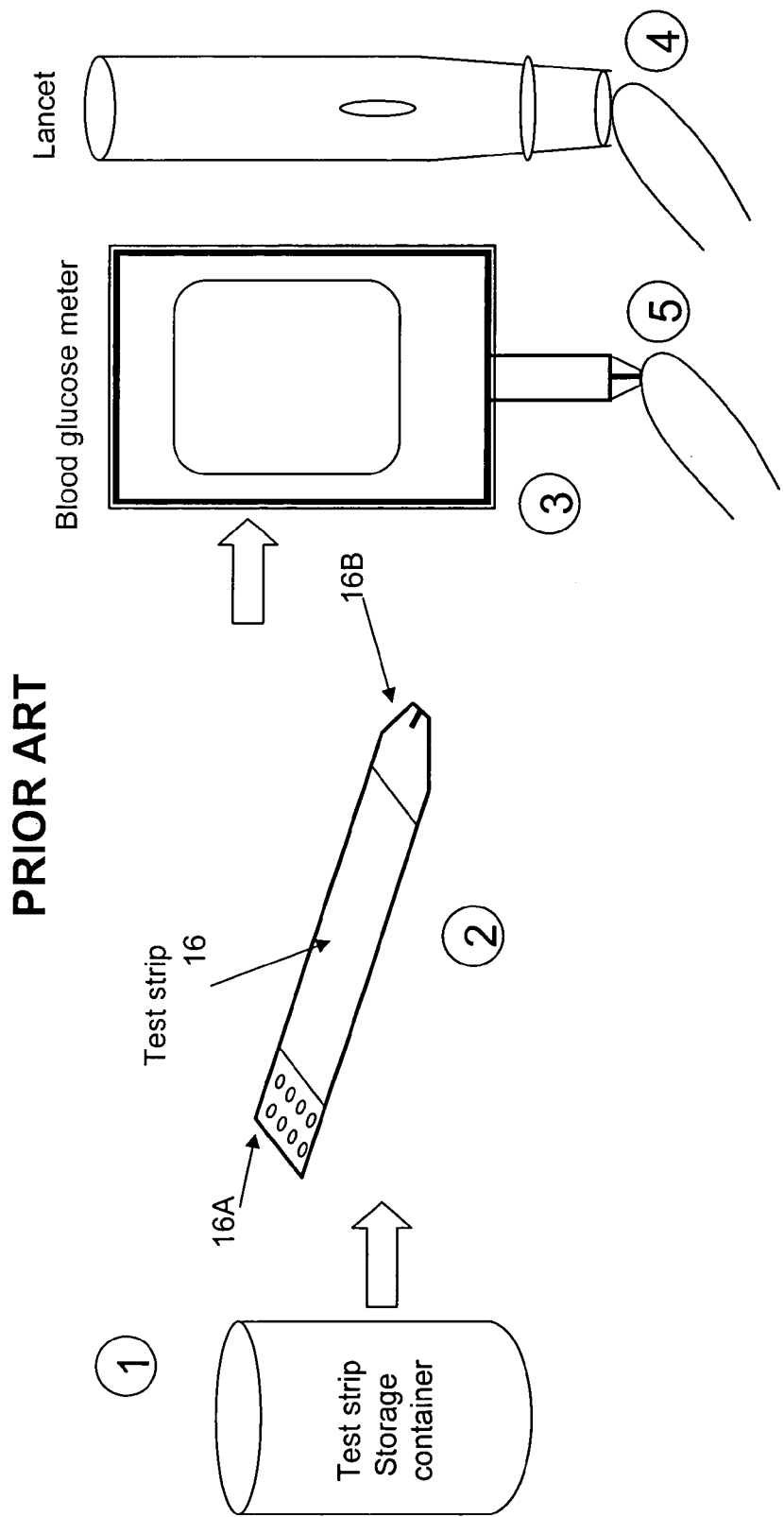

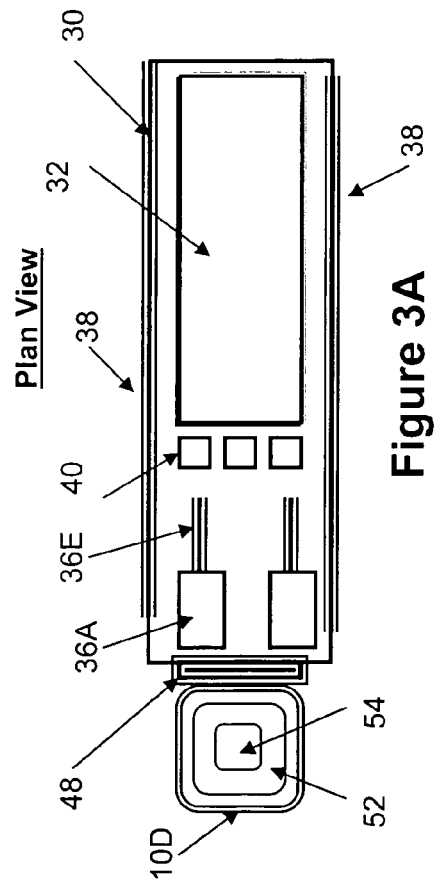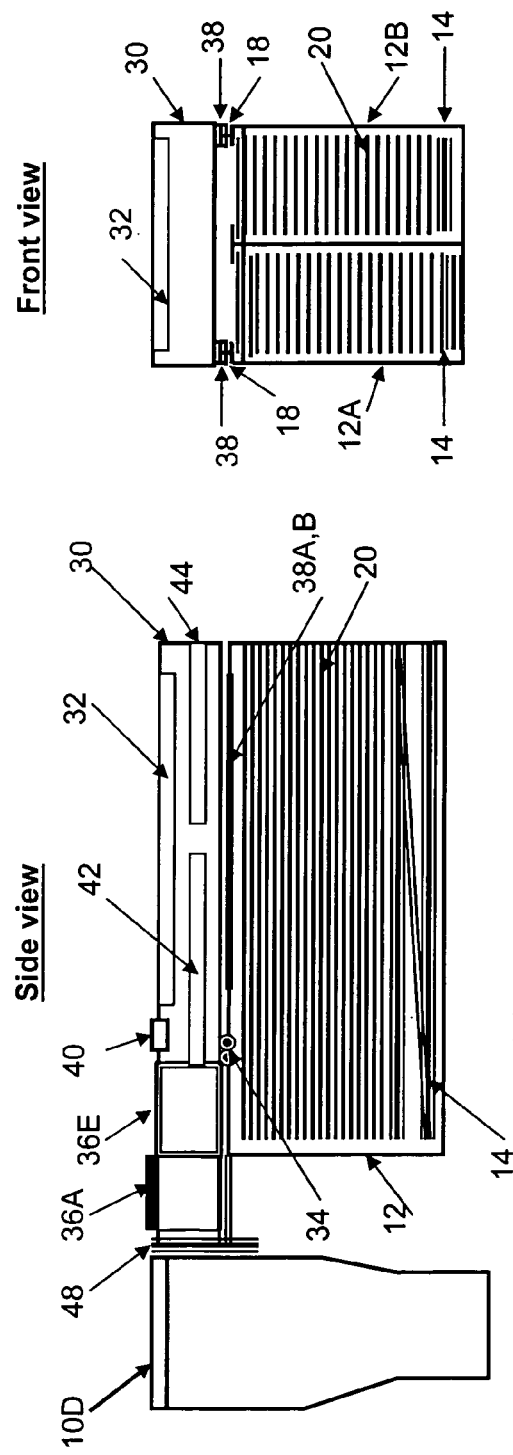

At step 100, integrating a test strip storage magazine with a blood glucose meter At step 102, integrating a test strip feed mechanism from the storage magazine with the blood glucose meter At step 104, integrating a lancet mechanism with the blood glucose meter At step 106, enabling releasing a test strip and automatically activating meter, when strip connects to meter contacts At step 108, enabling using the deployed strip for blood intake from the finger At step 110, enabling reading a glucose value from the meter At step 112, enabling activating a meter switch to display a graph with the current reading At step 114, enabling inserting a test strip storage magazine into the meter At step 116, enabling removing and replacing a used magazine with a new magazine At step 118, integrating a dual test strip feed mechanism from the dual storage magazine for use with the meter

Figure 4

INTEGRATED BLOOD GLUCOSE MEASURING DEVICE

CROSS REFERENCE

None

FIELD OF THE INVENTION

An integrated blood glucose measuring device is described. The device integrates a blood glucose meter, a test strip storage container, and a test strip feeding mechanism in the same device. In another embodiment the lancet mechanism is also integrated in the same device enabling the different items required in measuring blood glucose to be integrated in a single device.

BACKGROUND

People across the United States and around the world suffer from a metabolic disease called diabetes. For these people who suffer from diabetes and taking insulin, a blood glucose meter is used at home to monitor their blood glucose levels. The blood glucose level in their blood is measured and monitored at different times of the day on a regular basis. The blood glucose meter works with a test strip and a lancet.

At the time of the blood glucose measurement, a test strip is retrieved from a storage container. The test strip is about ⅜" wide and 1.5 inch long. The test strip has an electrical contact end and a blood intake end. The electrical contact end of the test strip is inserted in the meter to activate the meter. The lancet is then used to prick the finger and draw a droplet of blood. The blood intake end of the test strip sticking out of the meter is then touched to the finger for blood intake into the test strip. The meter, after a processing delay, provides a blood glucose reading in a display screen of the meter. The meter has logic to retain multiple readings and display them on demand and also transfer them to a computer for analysis.

There are about half a dozen companies that make blood glucose meters for use in both the home settings and in hospitals. These companies are Abbott Laboratories, Bayer Health Care, Life Scan, Roche, Nipro and Aga Matrix and they market many popular brands of blood glucose meters in different form factors. These companies also market the tests test strips that fit their meters as well as the lancets.

Typically, a blood glucose meter is 2 inches by 3 inches and ½ an inch thick in size. The lancet is like a pen about 5 inch long and around ½ an inch in diameter. The improvements by the industry in the prior art as described above have been to reduce the form-factor size of the meter device as well as improve the accuracy of the measurement. However, as illustrated in the Prior Art FIG. 1, the number of items and the steps required to measure the blood glucose levels have stayed the same.

It is the objective of the embodiments herein to make possible an integrated blood glucose measurement device that reduces the number of items a user would have to carry. It is also the objective to reduce the number of steps a user would have to perform and also to reduce the overall size of such an integrated blood glucose measurement device to make it easier to carry and use.

SUMMARY

An integrated blood glucose measuring device is described. The integrated device has blood glucose metering device, a test strip storage mechanism attachable to the metering device, and a test strip feeding mechanism for feeding a single test strip from the storage mechanism to the metering device ready for blood intake. The metering device, the test strip storage mechanism and the test strip feeding mechanism are integrated into a single device for blood glucose measurement.

In another embodiment, a lancet mechanism is attachable to a side of the metering device and thus the metering device, the test strip storage mechanism, the test strip feeding mechanism, and the lancet mechanism are integrated into a single device for blood glucose measurement.

The test strip storage mechanism may have dual compartments for storing a dual stack of measurement test strips for enhanced storage capacity in a compact size. Each compartment is sized to hold a stack of test strips. Each compartment has a spring device at the bottom of the compartment that pushes the test strips up to an area with guides at the top of the compartment that hold a top test strip in place for retrieval. The test strip storage mechanism is similar in some aspects to that as used in an ammunition magazine. In an ammunition magazine cylindrical shape bullets are stored that are pushed up into a firing chamber via a spring. In the embodiments described herein of the test strip storage mechanism, test strips that are flat and rectangular pieces of plastic are stored and are pushed up in position by a spring.

These and other aspects of the embodiments herein are further described in detail with the help of the accompanying drawings and the description, where similar numbers are used to identify the features of the embodiments.

BRIEF DESCRIPTION OF THE DRAWINGS

Some of the novel features of the embodiments will be best understood from the accompanying drawings, taken in conjunction with the accompanying description, in which similar reference characters refer to similar parts, and in which:

FIG. 1 shows block diagrams that illustrate features of the prior art for blood glucose measurement.

FIG. 3A-C are plan, side and elevation views respectively of a preferred embodiment of a glucose measurement device.

FIG. 4 is a method diagram that illustrates features of a preferred embodiment of the glucose measurement device.

DESCRIPTION

Introduction

As illustrated in Prior Art FIG. 1, to measure blood glucose, at step 1, a test strip 16 is retrieved from a storage container. The test strip 16 has a electrical connection end 16A and a blood intake end 16B. At step 2, the electrical end of the test strip is inserted into a meter with the blood intake end sticking out. At step 3, the meter senses the test strip and provides ready indication in the display window. A user then at step 4, uses a lancet to draw blood from a finger and at step 5, uses the finger with the blood to touch to the test strip. After a processing delay, the meter provides a reading of the blood glucose.

In prior art, this regimen of using a blood glucose meter is required and repeated multiple times in a day and these individual blood glucose measuring items of, test strips in a storage container, the meter, and the lancet, need to be carried with the user. The embodiments described herein provide improvements by integrating these different items into a single compact blood glucose measuring device, that reduces the number of items as well as the steps as described above in the prior art.

Figure 2A:
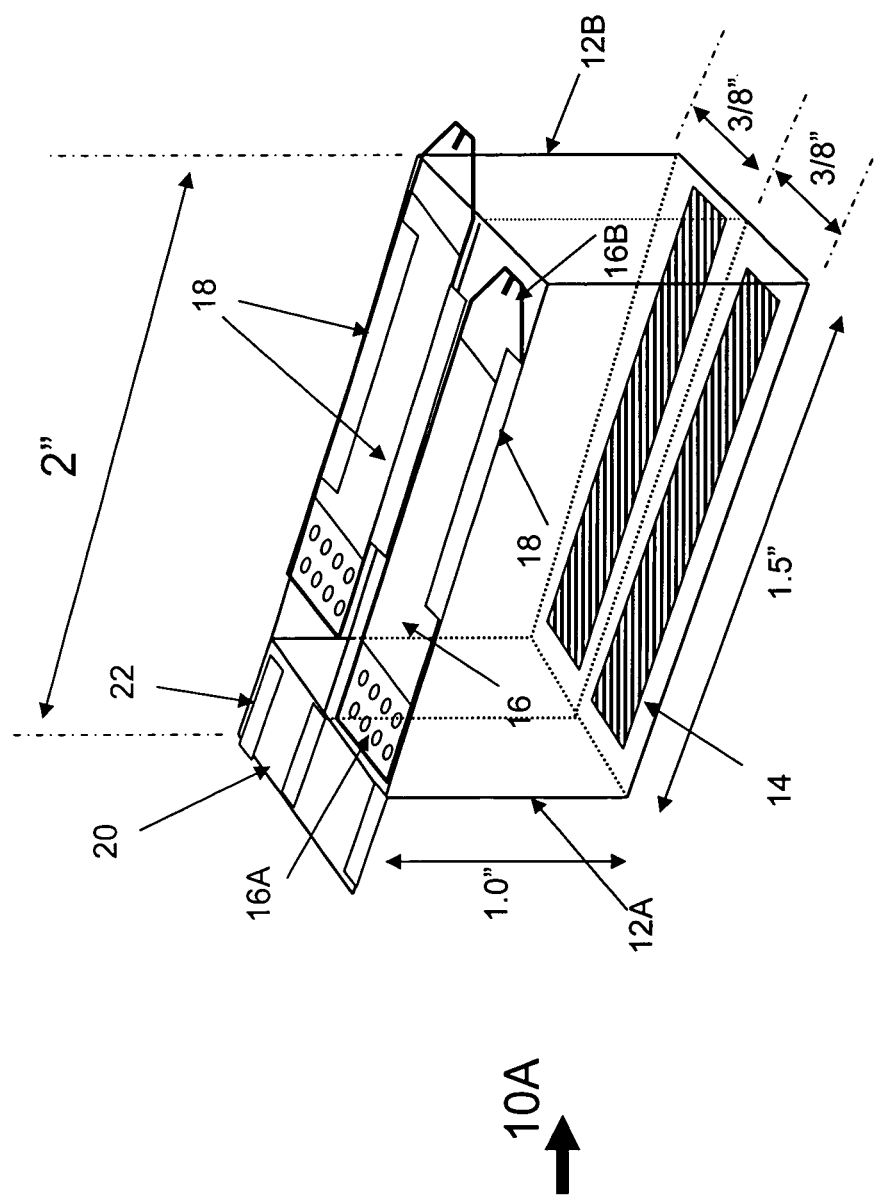
FIG. 2A is a block diagram that illustrates features of a preferred embodiment of a test strip storage magazine.

As shown in FIGS. 2A, 2B, 2C and 2D, there are different embodiments that are described. As shown in FIG. 2A, there is a test strip storage device 10A, that is used as a storage chamber for the test strips.

Figure 2B:
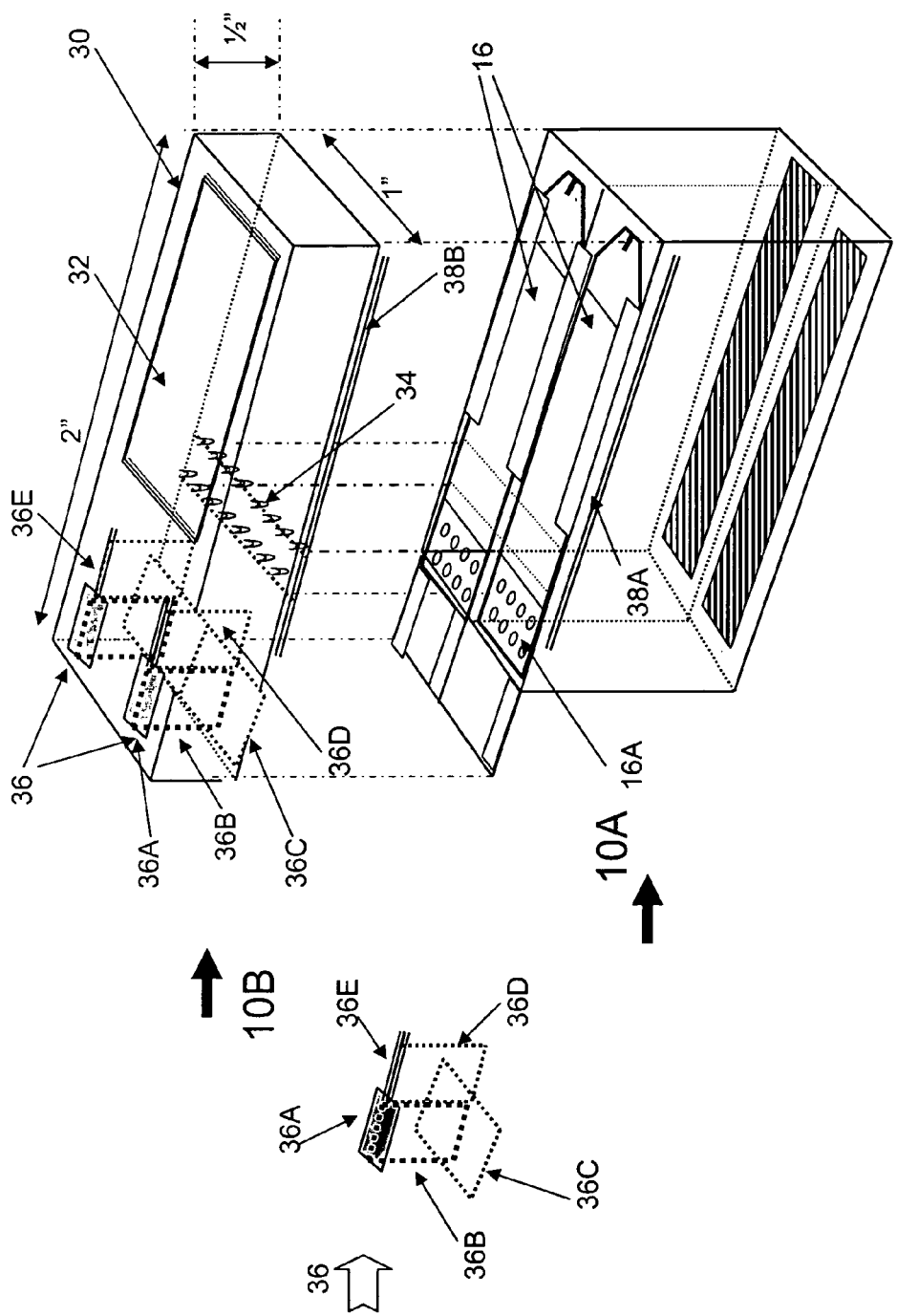
FIG. 2B is a block diagram that illustrates features of a preferred embodiment of integrating a test strip storage magazine with a meter.

As shown in FIG. 2B, a metering device 10B is attached to the storage device 10A. In this embodiment the test strips from the test strip storage 10A are automatically inserted into the meter 10B and the test strip is automatically connected to the meter device.

Figure 2C:
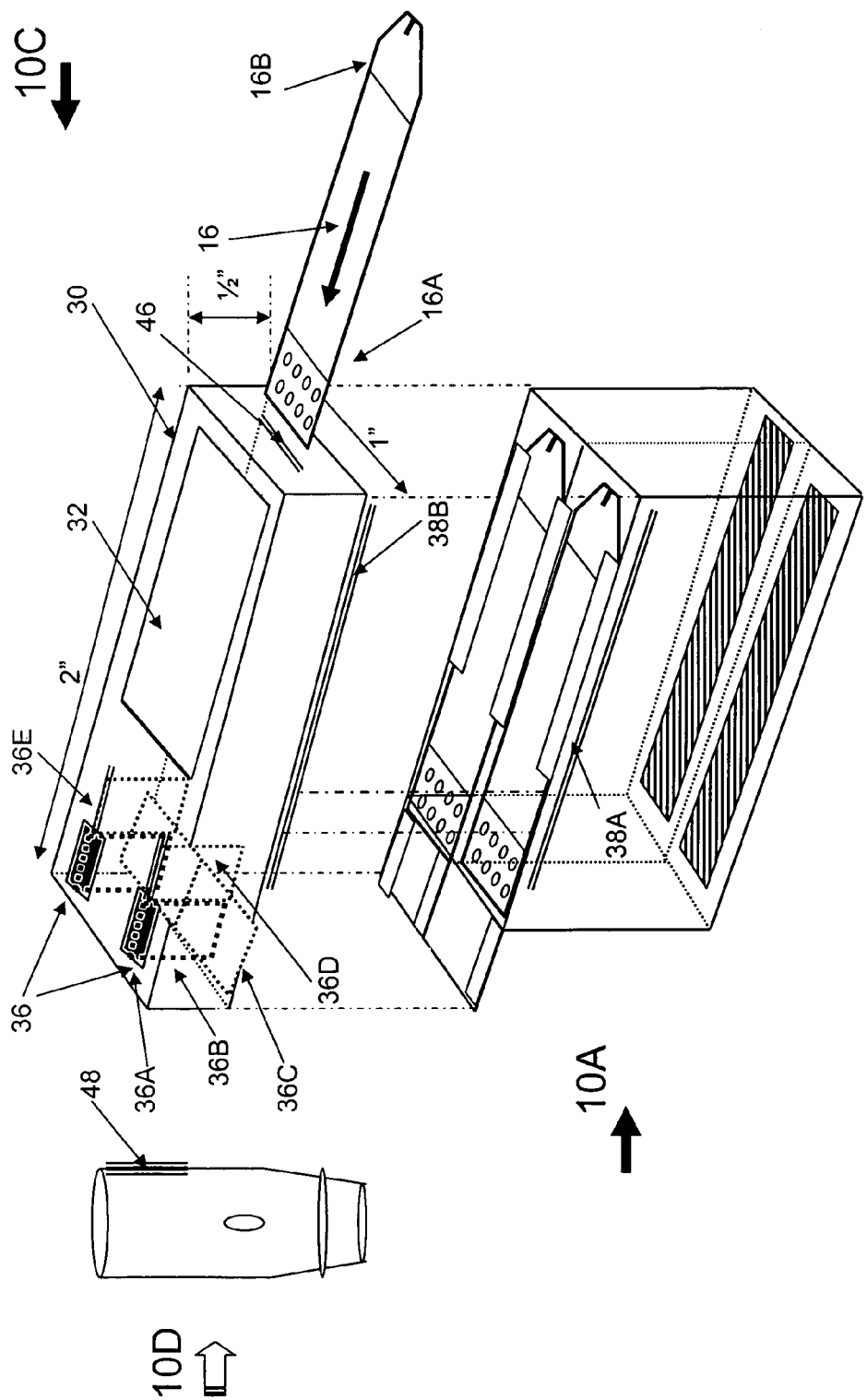
FIG. 2C is a block diagram that illustrates features of another embodiment of integrating a test strip storage magazine with a meter.

As shown in FIG. 2C, a metering device 10C is attached to the storage device 10A. In this embodiment, the test strip is retrieved from the storage device 10A and is then manually inserted into the meter device 10C.

Figure 2D:
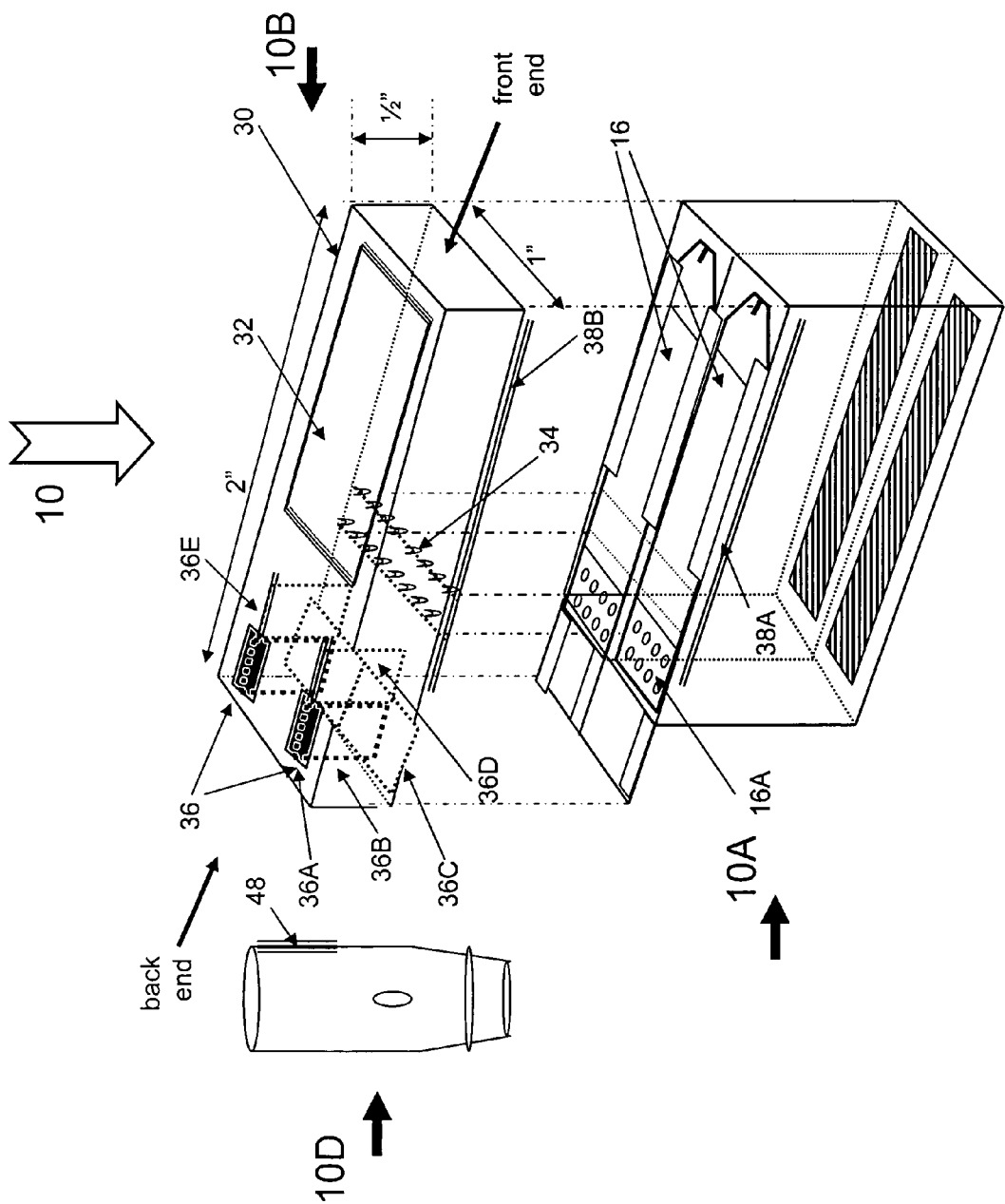
FIG. 2D is a block diagram that illustrates features of a preferred embodiment of integrating a test strip storage magazine with a metering device and a lancet mechanism.

As shown in FIG. 2D, a lancet device 10D may also be attached to the meter 10B. A lancet device 10D (not shown) may also be attached to meter device 10C in FIG. 2C.

In one embodiment, as shown in FIG. 2B, the test strip storage devices 10A and meter device 10B are integrated into a single device. In another embodiment, as shown in FIGS. 2C and 2D, all three devices, test strip storage device 10A, the meter device 10B or 10C, and the lancet device 10D are integrated in a single unit. In an alternative embodiment, as shown in FIG. 2C, the test strip is manually inserted into the meter device 10C, whereas, in the embodiment as in FIG. 2B, the test strip is automatically inserted into the meter.

Test Strip Storage Magazine 10A

As illustrated in FIG. 2A, the storage device 10A, has a left storage magazine 12A and a right storage magazine 12B positioned side by side and attached to each other. They are a single unit with two side by side or dual magazines. Each of the chambers 12A and 12B has a separate spring mechanism 14 at the bottom the chamber. Each of the chambers 12A and 12B may be individually stacked with test strips 16. The electrical end 16A of the test strip 16 is on one end and the blood intake end 16B on the other end of the chamber. On the top of the chambers 12A and 12B, there are positioned guides 18 that keep the top test strip of the stack in place and are used to guide the movement of the test strip as the test strip is pushed at the test strip end 16A. These guides may be built as integral to the chambers 12A and 12A as part of one fabrication or molding process. There are three guides 18, two on the outer side of the chambers 12A and 12B and one in the middle that is used for both these chambers, as the two chambers 12A and 12B have a one common wall or partition in the middle.

At the left end of the chambers, there is provided a platform 20 with its own guides 22 for the two chambers 12A and 12B. This platform and the guides are used to provide space for a push plate 36C of a feed mechanism 36 as shown and described later with the help of FIG. 2B.

As shown in FIG. 2A, the dual magazine 10A has guides 38A on each side of the magazine, where the corresponding guides 38B are on the meter 10B that enable the magazine 10A to be slid on the bottom side of the meter 10B with the help of guides 38A and 38B and securely attach to the meter as described with reference to FIG. 2B.

The magazine 10A may be made of any suitable plastic material and may be made of a clear or see through material that allows a user to visually see the stack of the test strips in each of the compartments 12A and 12B and to see how many test strips are left in the magazine and which one of these two magazines is nearly empty.

Alternatively, the magazine may be made of opaque material, and the quantity of the test strips in the magazine may be indicated by a count on the meter display. As each test strip is inserted into the meter a count may be kept, decremented, and displayed on the display 32 of the meter body 30.

All dimensions and sizes described herein are approximations or notional. A typical capacity of the magazine is likely to be 64 in number, 32 in each compartment. This capacity is based on the assumption that a test strip is likely to be 1/32 inch thick and the magazine is likely to be 1 and 1/4 inch in height allowing for a 1/4 inch space for the positioning of the spring in the magazine. Thus a one inch vertical space in the magazine would store 32 test strips in each compartment and dual magazine would store 64 test strips. However, the magazine may be sized to store 100 test strips by increasing the vertical space in the magazine.

The magazine 10A may have a detachable lid or a compartment cover in the form of a lid at the bottom of the magazine (not shown). The lid may be detached or removed to insert a stack of test strips and the lid may have a spring mechanism in the lid itself enabling the magazine to be filled in with test strips and closed from the bottom of the magazine.

Alternatively, the magazine 10A may be filled in from the top one test strip at a time. Which of these approaches for filling the magazine with the test strips may be used may depend on how the magazine is sold to the public. If the magazine is sold as a replacement magazine, then the magazine may come with a pre-stored supply of strips and the magazine is discarded when it is empty and new magazine used and inserted with the help of guides 38A and 38B into the meter body 30.

If the magazine 10A is sold as already integrated with the meter 10B, then the second method may be used to refill the magazine. In this method, the test strips that are sold for this purpose may be packed as stacks, enabling two packs of test strips to be dropped in the magazine from the bottom and the lid with the spring pushed in and securely locked in place.

The magazine spring may be similar to what is used in ammunition magazines which pushes up the stack of bullets in the magazine, as each bullet is positioned in the firing chamber. Alternatively, the spring may be of a different design such as a helical coiled spring. The design of the spring enables the last test strip of the stack to be pushed all the way up to the guides 18.

What has been described above is a preferred embodiment of the test strip storage magazine 10A and many other embodiments may be possible and are not ruled out.

Integration of Meter 10B and Test Strip Storage Magazine 10A

As shown in FIG. 2B, a meter 10B is shown positioned on top of the storage magazine 10A. The meter 10B has a guide 38 with guide members 38B on the meter and guide member 38A on the storage magazine 10A, that enable the magazine 10A to be inserted into the meter 10B to become and function as one integrated unit.

The meter 10B has a meter body 30, with a display window 32 on the top side, electrical contacts 34 on the underside of the body 30, which connect the test strip 16 to the meter when the test strip is pushed forward in position with the help of a feed mechanism 36. There are two individual test strip feed mechanisms for two magazines 12A and 12B respectively.

Test Strip Feed Mechanism 36

With reference to FIG. 2B, a test strip feed mechanism 36 is described. The mechanism 36 has a slide member 36A, a vertical member 36B, a slide plate 36C, a spring 36D and a guide groove 36E in the meter body. The slide member 36A is positioned on top of the meter body 30 and has a vertical member 36B attached to the slide member 36A. The vertical member 36B is attached to a horizontal plate 36C that is positioned on the plate 20 of the magazine 10A, when the magazine 10A and the meter 10B are integrated as one unit.

A groove 36E on the meter body 30 enables the slide 36A to be moved forward against a spring resistance 36D that enables the slide plate 36A and thus the slide plate 36C to automatically return to the original position.

When the slide plate 36A is slid forward the plate 36C engages and moves the test strip 16 forward in the storage compartment 12A or 12B, depending on which of the two slides 36 is used.

As shown in FIG. 2B, the test strip feed mechanism 36 moves or slides the test strip 16 forward a fixed predetermined distance, until the test strip's electrical contact 16A make electrical contact with electrical contacts 34 positioned on the underside of the meter body 30. At that position of the test strip 16, in the magazine 10A, the blood intake end 16B of the test strip 16 extends out of the magazine body by a distance that enables the end 16B to be used for blood intake.

The test strip feed mechanism 36 may be of a different design than what is described above and other designs are not ruled out. For example, the two slide members 36A for two magazines may be positioned on the side of the meter body 30 as opposed to on the top as had been described above. The test strip feed mechanism 36 is preferably used by a thumb as the integrated device with meter 10B and the magazine 10A is held in the palm of the hand.

The Meter Body 30

The contacts 34 at the underside of the meter body 30 are dual series of contacts, one set of contacts for each of the two test strips. The meter 30 senses only one of these contacts to be energized depending upon which one of the test strips is used from the magazine. The contacts 34 are spring loaded and permit the sliding of the test strip 16, while at the same time make electrical contact between the meter 30 and the test strip 16. Thus, the contacts 34 make electrical contact with only one test strip contact 16A at one time. If by mistake, both sets of contacts are energized then the meter would indicate a fault.

The meter body 30 is sized to be approx. one inch wide, ½ an inch high and about 2 inch long. The meter body 30 sits on top and is attached onto the magazine 10A. The magazine 10A thickness is sized to be ⅜" plus ⅜" plus a slack margin plus thicknesses of the three wall of the magazine. This thickness of the magazine may equal ⅞". An additional ⅛ inch may be used for guides 38 with two members 38A on the magazine and member 38B on the meter body, thus enabling the width of the meter body 30 and the storage 10A to be the same and thus an overall width of the integrated device to be one inch wide. However, the width of the meter 30 and the magazine 10A may be different than these sizes and may be different from each other.

As shown in FIG. 2A, the test strips are 1.5 inch long, the length of the plate 20 may be ½", thus making the length of the magazine 10A to be approximately 2.0". As shown in FIG. 2B, thus, a meter body 30 attached to the top of the storage magazine 10A may also be 2" long. However, the size of the meter body 30 may be different then these dimensions.

There is clearance space between the test strip magazine 10A and the meter 10B, when the two are attached to each other as had been described above. This clearance space accommodates the electrical connections 34 of the meter body 30 and their movement on top of the test strip, as the test strip is pushed out from the magazine 10A. This clearance space also accommodates the guides 18 that hold the top test strip in place. This clearance space may be $\frac{1}{16}^{th}$ of an inch and may be as much as $\frac{1}{8}^{th}$ of an inch. The height of the meter body 30 may be ½", thus the height of the integrated device may be close to 2" as well.

Thus the integrated device would have an overall dimension of 2" long, 1" wide and 2" high. Such a integrated device may provide as much as ⅞" by ⅞" display area on the top of the meter body. As shown in plan view FIG. 3A, the meter body 30 may also have three switches 40 on the top side of the meter body 30 to operate different functions of the meter 10B. Prior art enables such small size meters to be fabricated with the modern electronics. An example is the Bayer meter in the approximate form factor of a USB key.

The orientation of the meter body 30 and the orientation of the test strip storage magazines 12A and 12B, make for convenient alignment and a desirable form-factor. However, the magazine 10A and the meter 10B may be attached to each other in a different orientation of arrangement and such orientations are not ruled out.

Alternatively, the meter body 30 may be made in a size that would be suitable for the embodiments herein. The magazine 10A may be of ¾" wide to accommodate two stacks side by side, 1 inch high and 1.5 inch long to accommodate the size of test strips 16 that are ⅜" wide and 1.5 inch long. The meter body may be ½ inch high, a 1" inch wide and 2 inch long. The lancet 10D may be ¾" square and 1.5" high. Thus the size of an integrated device would be approximately 1" wide, 1.5 inch high and 3 inch long. The quantity of test strips that would be stored in the magazine would be 64 in the two stacks, assuming the thickness of the test strip 16 is increased to 1/32 inch for the embodiments herein.

Manual Feed of Test Strip into the Meter 10C

As shown in FIG. 2C, in this embodiment, the meter 10C with meter body 30 does not have electrical contacts 34 on the underside of meter body 30, as in 10B, but has the electrical contacts inside the meter body 30 that are connected to the test strip 16, when the test strip 16 is inserted in the meter body 30 via an opening 46 on the front of body 30. In this embodiment, the test strip 16 is pushed out from the test strip magazine 10A with the help of the test strip feed mechanism 36. The test strip is then manually pulled out and removed from the magazine 10A and then manually inserted in opening 46 on the meter body 30.

Meter 10B Integrated with Test Strip Magazine 10A and Lancet 10D

As shown in FIG. 2D, a lancet mechanism 10D is sized to be attachable to the meter 10B. The lancet mechanism 10D has attachment guides 48 that attach to the backend of the body 30 of the meter 10B.

The prior art lancet mechanism is made in the form factor of a pen to make it convenient to hold and use. The mechanism in such a lancet may also be made in the form factor as desired in this embodiment. The form-factor of the lancet 10D may be ¾" square and 2 inches long. Such a form factor would attach at the back end of the meter body 30, as shown in FIGS. 3A and 3B, the plan and side views respectively. Alternatively the lancet mechanism 10D may also attach (not shown) to the meter body in the front and side of the meter body 30.

In some embodiments the all three devices, the test strip magazine 10A, the meter 10B and the lancet mechanism 10D may come pre-built at the factory as one integrated unit. Such a glucose measurement device 10 is shown in FIG. 2D.

The embodiments 10A, 10B, and 10D are further illustrated with the help of a plan view as in FIG. 3A, a side view as in FIG. 3B and a front view as shown in FIG. 3C. As shown in FIG. 3A, the arm and release mechanisms 52 and 54 of the lancet 10D may be positioned on top of the lancet mechanism 10D.

As illustrated with the help of FIG. 3A, in the plan view, a meter body 30, a display window 32, attachment mechanism 38 that attaches the meter body 30 with the test strip magazine 10A, the slide plate 36A and slide channel 36E of the test strip feed mechanism 36, in the meter body 30 are shown. Further switches 40 that operate the meter electronics are also shown in their preferred positions and a preferred placement of the lancet mechanism 10D via attachment 48 to the meter body 30.

As illustrated with the help of FIG. 3B, in the side view, the meter body 30, the meter display window 32, the switches 40, the meter electronics 42, and the battery 44 are shown. Also shown are the test strip feed mechanism members 36A and 36E. Electrical contacts 34 on the underside of meter body 30 are also shown that make contact with the end 16A of the test strip 16, when the test strip 16 is pushed forward with the help of the test strip feed mechanism 36. The magazine 10A, with a spring 14 at the bottom of the magazine compartment 12 is also shown. Further a stack 20 of test strips 16 is shown and further the guide attachment mechanism 38 with parts 38A and 38B that are attach the magazine 10A to the meter body 30 are also shown.

As illustrated with the help of FIG. 3C, in the front view, is shown the meter body 30, the display window 32, the left and right magazines 12A and 12B respectively with their individual springs 14, and stacks 20 of the test strips 16. Also the guide 18 for the test strip 16 on the top end of the magazines 12A and 12B are shown. Further the guide 38 that attaches the magazine 10A with the meter body 10B is also shown.

The guides 18 are positioned on top of the magazine with a clearance equal to or slightly greater than the thickness of the test strip 16. The test strip 16 thickness is usually $1/64^{th}$ of an inch thick. However, to make the test strip 16 to be easily engaged and pushed forward by the mechanism 36, the test strip 16 thickness may be $1/32"$. The test strip 16 has a plastic base on which the test strip parts of electrical conductors and the blood intake gauze are built on. That base thickness of the test strip may be increased without affecting the manufacturing process of the rest of the test strip 16.
The Guide Mechanisms 38 and 48

There are two guide and attachment mechanisms 38 and 48 that are used in the embodiments herein. The guide mechanism 38 is used to attach the storage magazine 10A to the meter 10B. The guide mechanism 48 is used to attach the lancet mechanism 10D to the meter 10B or 10C.

These guide mechanisms are of tongue and groove type providing for a snug fit and attachment between these different assemblies of the integrated glucose measuring device. As a simplified illustration the guide may include a female part of the guide in a U shape channel and the male part of the guide in a T shape channel. The vertical part of the T shape channel is slid into the opening of the U shape channel. The guides may be of another design and are not ruled out.

There is also a locking mechanism that would lock the devices together. There are many prior art guide and locking mechanisms. No specific claim is made to any guide and lock mechanism for integrating these separate devices of the meter, the lancet and the test strip magazine.

A blood glucose measuring device has a blood glucose metering device, a glucose metering test strip storage mechanism attached to the metering device, and a test strip feeding mechanism for feeding a single test strip from the storage mechanism directly into the metering device. The metering device, the test strip storage mechanism and the test strip feeding mechanism are integrated into a single device for blood glucose measurement.

The blood glucose measuring device has a lancet mechanism attached to a side of the metering device. The metering device, the storage mechanism, the test strip feeding mechanism, and the lancet mechanism are integrated into a single device for blood glucose measurement.

The storage mechanism uses a rectangular shaped compartment for storage of a stack of test strips. The compartment has a back side and a front side, where a electrical contact side of the test strip is positioned on the back side and a blood intake side is positioned on the front side. The compartment has a bottom side with a spring mechanism for pushing the test strips up and a top side for holding a single test strip for use for blood intake, the top side has guides for holding and guiding a single test strip from the stack of test strips, when the feeding mechanism is used to feed the test strip for blood intake.

The storage mechanism has dual compartments for storing a dual stack for enhanced storage capacity, where each compartment is sized to hold multiple test strips in a stack.

The blood glucose metering device, with electrical contacts for a metering test strip, has those electrical contacts positioned on the metering device to make electrical contact with the test strip, when the test strip is extended out of the storage mechanism for blood intake.

The blood glucose measuring device has a feeding mechanism that has a spring loaded lever that pushes a top positioned test strip in the storage chamber forward a distance that enables (i) the test strip's electrical contacts to make electrical contacts with the metering device, and (ii) extend the blood intake side of the test strip out of the storage mechanism for blood intake.

There are two independent feeding mechanism when the storage mechanism has dual storage compartments, one each for each compartment.

The spring loaded lever has a horizontally positioned on a top side of the meter, a slide plate, a slide guide, a vertical member attached to underneath the slide plate, and a horizontal member attached to the vertical member, wherein the horizontal member pushes a single test strip out of the storage mechanism.

The metering test strip is of a thickness that enables the test strip feeding mechanism to engage one test strip at a time for feeding from the storage mechanism.

The lancet mechanism is of dimension in length and girth size that would be attachable to the back side of the metering device and fit within in the contour of the measuring device.

A blood glucose measuring device has a blood glucose metering device, a glucose metering test strip storage mechanism attachable to the metering device, and a manual test strip feeding mechanism for feeding a single test strip from the storage mechanism for blood intake into the meter by manually removing the test strip from the storage and inserting the test strip in the meter, the metering device, the test strip storage mechanism and the test strip feeding mechanism are integrated into a single device for blood glucose measurement.

The blood glucose measuring device has a lancet mechanism attachable to a side of the metering device. The metering device, the storage mechanism, the test strip feeding mechanism, and the lancet mechanism are integrated into a single device for blood glucose measurement.

The storage mechanism uses a rectangular shaped compartment for storage of a stack of test strips. The compartment has a back side and a front side, where a electrical contact side of the test strip is positioned on the back side and a blood intake side is positioned on the front side. The compartment has a bottom side with a spring mechanism for pushing the test strips up and a top side for holding a single test strip for use for blood intake, the top side has guides for holding and guiding a single test strip from the stack of test strips, when the feeding mechanism is used to feed the test strip for blood intake.

The storage mechanism has dual compartments for storing a dual stack for enhanced storage capacity, where each compartment is sized to hold multiple test strips in a stack.

Mode of Operation

A user first examines the test strip magazine 10A of the device 10 to see the clear plastic magazine 12A and 12B and sees that there is a supply of test strips in the magazine 10A and which magazine 12A or 12B he/she would like to use.

Then a user uses the lancet 10D to arm and deploy to prick his/her finger. Then the user turns the device 10B around and slides the lever 36A of mechanism 36 to deploy a test strip 16 from either left or right chamber. In some embodiments, the lancet 10D may be mounted in the front and side of the meter 10B, thus avoiding this step of turning the meter 10B around.

The test strip 16 is deployed and the meter 10B is activated automatically when the electrical connection 34 is made between the test strip 16 and the meter 30. The user touches the finger to test strip end and waits for the meter to provide a reading. The user pulls and removes the test strip 16 and discards it. The user presses a switch 40 to examine the readings via a graph. Alternatively as in embodiment as shown in FIG. 2C, the test strip 16 is manually pulled from the magazine 10A and then manually inserted in the slot 46 of the meter body 30.

When the test strip magazine 10A is empty of test strips, the lid at the bottom of the magazine may be opened to provide access to the inside of the magazine and stacks of the test strips may be dropped in the magazine 10A and the lid with the spring would be closed.

The meter 10B may also include memory and logic to store and display a daily and a weekly graph of the blood glucose readings on the display of the meter. The logic would be built in or programmed in the integrated circuit chips that would be used in the meter 10B.

Prior art advances in miniaturizing of the electronic devices make such features possible in small electronic devices as in meter device 10B possible. A bar graph may be shown for a day or a week, along with horizontal lines indicating desirable and mean blood glucose values. In prior art, such analysis was done via porting the data from the meter device 10B to a computer with the software to be able to receive and analyze such data. Having logic and memory in the device 10B enables that feature to be available on the fly anywhere any time or when a reading is taken with the device 10.

Method of Operation

As illustrated in FIG. 4, method for using the device 10 has the following steps where all the steps may not be used or used in the order specified:

At step 100, integrating a test strip storage magazine 10A with a blood glucose meter 10B.

At step 102, integrating a test strip feed mechanism 36 from the storage magazine 10A with the blood glucose meter 10B.

At step 104, integrating a lancet mechanism 10D with the blood glucose meter 10B.

At step 106, enabling releasing a test strip and automatically activating meter, when strip connects to meter contacts.

At step 108, enabling using the deployed strip for blood intake from the finger.

At step 110, enabling reading a blood glucose value from the meter.

At step 112, enabling activating a meter switch to display a graph with the current reading.

At step 114, enabling inserting a test strip storage magazine into the meter.

At step 116, enabling removing and replacing a used magazine with a new magazine.

At step 118, integrating a dual test strip feed mechanism from the dual storage magazine for use with the meter.

In summary, the preferred embodiments are on a blood glucose measurement device 10 that integrates the measurement test strip storage 10A and the meter 10B in a single compact device, enabling test strips to be stored, retrieved and fed into the meter without being touched by the human in a single action. In another embodiment, a compact version of the lancet mechanism 10D is attached to an end of the meter 10B body, providing all the three elements, lancet 10D, test strips 10A and the meter 10A to be integrated in a single compact device, that is believed, would be easy to carry, easy to store in personal possessions, and easy to use many times in a day.

While the particular invention, as illustrated herein and disclosed in detail is fully capable of obtaining the objective and providing the advantages herein before stated, it is to be understood that it is merely illustrative of the presently preferred embodiments of the invention and that no limitations are intended to the details of construction or design herein shown other than as described in the appended claims.

The invention claimed is:

1. A blood glucose measuring device, comprising:
a blood glucose metering device, wherein the metering device has a first side and a second side, wherein the first side has a display screen and the second side has a dual set of spring loaded electrical contacts and a metering test strip for use with the metering device;
a test strip storage mechanism body, wherein the mechanism body has dual compartments, and wherein the dual compartments are positioned side by side in the mechanism body for storing a dual stack of test strips, the mechanism body is attachable to the second side of the metering device and enables the mechanism body to be removed and attached from and to the second side of the metering device, the mechanism body allows a view of the test strips in the dual compartments;

a test strip feeding mechanism for feeding a single test strip from one of the dual compartments in the storage mechanism for use with the metering device, wherein the feeding mechanism feeds into the metering device the single test strip from one of the dual compartments, the single test strip makes electrical contact with one of the dual sets of springs on the second side of the metering device, the metering device, the test strip storage mechanism and the test strip feeding mechanism are integrated into a single device for blood glucose measurement.

2. The blood glucose measuring device, as in claim 1, further, comprising:
   a. a lancet mechanism attached to a side of the metering device;
   b. the metering device, the storage mechanism, the test strip feeding mechanism, and the lancet mechanism are integrated into a single device for blood glucose measurement.

3. The blood glucose measuring device, as in claim 1, the storage mechanism body comprising:
   a. the storage mechanism body uses a substantially rectangular shaped dual compartments for storage of stacks of test strips;
   b. the compartments have a back side and a front side, where an electrical contact side of the test strip is positioned on the back side and a blood intake side of the test strip is positioned on the front side.

4. The blood glucose measuring device, as in claim 1, further comprising:
   each compartment of the storage mechanism body is sized to hold multiple test strips in a stack.

5. The blood glucose measuring device, as in claim 1, further comprising:
   the blood glucose metering device, with electrical contacts for the metering test strip, has those electrical contacts positioned on the metering device to make electrical contact with the test strip, when the test strip is extended out of the storage mechanism for blood intake.

6. The blood glucose measuring device, as in claim 1, further comprising:
   the feeding mechanism has a spring loaded lever that pushes a top positioned test strip in the storage chamber forward a distance that enables (i) the test strip's electrical contacts to make electrical contacts with the metering device, and (ii) extend a blood intake side of the test strip out of the storage mechanism for blood intake.

7. The blood glucose measuring device, as in claim 4, further comprising:
   two independent test strip feeding mechanisms, one each for each compartment.

8. The blood glucose measuring device, as in claim 6, further comprising:
   the spring loaded lever is positioned on a side of the meter, a slide plate, a slide guide, a vertical member attached to underneath the slide plate, and a horizontal member attached to the vertical member, wherein the horizontal member pushes a single test strip out of the storage mechanism.

9. The blood glucose measuring device, as in claim 1, further comprising:

the metering test strip is of a thickness that enables the test strip feeding mechanism to engage one test strip at a time for feeding from the storage mechanism.

10. The blood glucose measuring device, as in claim 2, the lancet mechanism, further, comprising:
    the lancet mechanism is of dimension in length and girth size that would be attachable to the back side of the metering device and fit within in the contour of the measuring device.

11. A blood glucose measuring device, comprising:
    a blood glucose metering device, wherein the metering device has a first side and a second side, wherein the first side has a display screen and the second side has a set of spring loaded electrical contacts and a metering test strip for use with the metering device;
    a test strip storage mechanism body, wherein the mechanism body that has dual compartments for storing a dual stack of test strips, the mechanism body is attachable to the second side of the metering device and enables the mechanism body to be removed and attached from and to the second side of the metering device, the mechanism body allows a view of the test strips in the dual compartments;
    a manual test strip feeding mechanism for feeding a single test strip from the storage mechanism for blood intake into the metering device by manually removing the test strip from the storage mechanism and inserting the test strip in the metering device, wherein the test strip makes electrical contact with the set of springs on the second side of the metering device, the metering device, the test strip storage mechanism and the test strip feeding mechanism are integrated into a single device for blood glucose measurement.

12. The blood glucose measuring device, as in claim 11, further, comprising:
    a. a lancet mechanism attachable to a side of the metering device;
    b. the metering device, the storage mechanism, the test strip feeding mechanism, and the lancet mechanism are integrated into a single device for blood glucose measurement.

13. The blood glucose measuring device, as in claim 11, the storage mechanism comprising:
    a. the storage mechanism uses a substantially rectangular shaped dual compartments for storage of stacks of test strips;
    b. the compartments have a back side and a front side, where an electrical contact side of the test strip is positioned on the back side and a blood intake side is positioned on the front side.

14. The blood glucose measuring device, as in claim 11, further comprising:
    each compartment of the storage mechanism is sized to hold multiple test strips in a stack.

15. The blood glucose measuring device, as in claim 1, further comprising:
    a. the metering device has a display side and a non-display side;
    b. the non-display side of the metering device has electrical contacts, for making electrical contact with the metering test strip, when the test strip storage mechanism body is attached to the non-display side of the metering device.

16. The blood glucose measuring device, as in claim 15, further comprising:
    the non-display side of the metering device has exposed spring loaded electrical contacts, for making electrical contact with the metering test strip, when the test strip storage mechanism body is attached to the non-display side of the metering device.

17. The blood glucose measuring device, as in claim 1, further comprising:

the compartment has a bottom side with a spring mechanism for pushing the test strips up and a top side for holding a single test strip for use for blood intake, the top side has guides for holding and guiding a single test strip from the stack of test strips, when the feeding mechanism is used to feed the test strip for blood intake.

18. The blood glucose measuring device, as in claim 1, further comprising:

the test strip storage mechanism body has dual compartments for storing a dual stack of test strips, where the stacks of test strips are positioned side by side and the mechanism body is substantially sized in width and length to a twice of a width of the test strip and a length of a test strip respectively and in a height the mechanism body is sized to store up to fifty test strips in a one of the dual stacks of test strips;

the metering device is substantially sized to attach to the storage mechanism body.

19. The blood glucose measuring device, as in claim 4, further comprising:

the test strip storage mechanism body has dual compartments for storing a dual stack of test strips, where the stacks of test strips are positioned side by side and the mechanism body is substantially sized in width to a twice of a width of the test strip and in a height to store up to fifty test strips in a one of the dual stacks of test strips;

the metering device is substantially sized to attach to the storage body.

20. The blood glucose measuring device, as in claim 13, further comprising:

the compartment has a bottom side with a spring mechanism for pushing the test strips up and a top side for holding a single test strip for use for blood intake, the top side has guides for holding and guiding a single test strip from the stack of test strips, when the feeding mechanism is used to feed the test strip for blood intake.

* * * * *